(12) United States Patent
Matsumoto et al.

(10) Patent No.: US 10,327,788 B2
(45) Date of Patent: Jun. 25, 2019

(54) SURGICAL JIG, VERIFICATION JIG, AND METHODS FOR PRODUCING THESE JIGS

(71) Applicants: ONO & Co., Ltd., Tokyo (JP); Nozomu Matsumoto, Fukuoka (JP)

(72) Inventors: Nozomu Matsumoto, Fukuoka (JP); Hidenori Ono, Tokyo (JP); Hisayuki Sugiyama, Kanagawa (JP); Toru Matsumoto, Tokyo (JP)

(73) Assignees: ONO & CO., LTD., Tokyo (JP); NOZOMU MATSUMOTO, Fukuoka (JP)

( * ) Notice: Subject to any disclaimer, the term of this patent is extended or adjusted under 35 U.S.C. 154(b) by 604 days.

(21) Appl. No.: 14/894,246

(22) PCT Filed: May 20, 2014

(86) PCT No.: PCT/JP2014/063309
§ 371 (c)(1),
(2) Date: Nov. 25, 2015

(87) PCT Pub. No.: WO2014/192586
PCT Pub. Date: Dec. 4, 2014

(65) Prior Publication Data
US 2016/0128705 A1 May 12, 2016

(30) Foreign Application Priority Data

May 29, 2013 (JP) .................................. 2013-112773

(51) Int. Cl.
*A61B 17/17* (2006.01)
*H04R 25/00* (2006.01)
(Continued)

(52) U.S. Cl.
CPC .......... *A61B 17/1739* (2013.01); *A61F 11/00* (2013.01); *G05B 15/02* (2013.01);
(Continued)

(58) Field of Classification Search
CPC combination set(s) only.
See application file for complete search history.

(56) References Cited

U.S. PATENT DOCUMENTS 4,774,933 A 10/1988 Hough et al.
4,791,919 A 12/1988 Elloy et al.
(Continued)

FOREIGN PATENT DOCUMENTS

EP 2564792 3/2013
JP 61-209654 9/1986
(Continued)

OTHER PUBLICATIONS

Extended European Search Report for PCT-JP2014063309 dated May 12, 2017.
(Continued)

*Primary Examiner* — Sameh R Boles
(74) *Attorney, Agent, or Firm* — Smith, Gambrell & Russell, LLP.

(57) ABSTRACT

There are provided a surgical jig (24) which is directly used during surgery to make it possible to accurately recognize a position where a recess (44, 46) is to be formed in the surface of a surgical target bone (14) of a patient; and a verification jig (34) which is directly used during surgery to make it possible to precisely verify whether or not the recess (44, 46) formed in the surface of the surgical targeted bone (14) of the patient is of a required shape.

The surgical jig (24) has an inner surface (26) matching the surface shape of the surgical target bone (14) of the patient, and a penetrating opening (30, 32) formed in correspondence with a site where the recess (44, 46) is to be formed. The verification jig (34) has a protrusion (40, 42) protruding from an inner surface (36) thereof in correspondence with the recess (44, 46) to be formed.

3 Claims, 6 Drawing Sheets

(51) Int. Cl.
  *A61F 11/00* (2006.01)
  *G05B 15/02* (2006.01)
  *A61B 34/10* (2016.01)
  *A61B 17/00* (2006.01)

(52) U.S. Cl.
  CPC ......... H04R 25/604 (2013.01); H04R 25/606 (2013.01); *A61B 17/1771* (2016.11); *A61B 2017/00526* (2013.01); *A61B 2034/108* (2016.02); *H04R 2460/13* (2013.01)

(56) References Cited

U.S. PATENT DOCUMENTS

| | | | |
|---|---|---|---|
| 9,125,693 | B2 | 9/2015 | Sugawara et al. |
| 2006/0058819 | A1 | 3/2006 | Kasic, III |
| 2009/0312801 | A1 | 12/2009 | Lemoine et al. |
| 2011/0243356 | A1 | 10/2011 | Koike et al. |
| 2012/0116316 | A1* | 5/2012 | Schutz ............ A61M 39/0247 604/175 |
| 2013/0018378 | A1 | 1/2013 | Hananouchi et al. |
| 2013/0041381 | A1 | 2/2013 | Clair |
| 2014/0096369 | A1 | 4/2014 | Matsumoto et al. |

FOREIGN PATENT DOCUMENTS

| | | |
|---|---|---|
| JP | 2009-61132 | 3/2009 |
| JP | 4423362 | 3/2010 |
| JP | 2010-75394 | 4/2010 |
| WO | 2006/127486 | 11/2006 |
| WO | 2011-149106 | 1/2011 |
| WO | 2012-169642 | 12/2012 |

OTHER PUBLICATIONS

Supplementary partial European Search Report for PCT-JP2014063309 dated Dec. 23, 2016.

* cited by examiner

SURGICAL JIG, VERIFICATION JIG, AND METHODS FOR PRODUCING THESE JIGS

TECHNICAL FIELD

This invention relates to a surgical jig for surgery for forming a recess in the surface of a bone of a patient targeted for surgery (may hereinafter be referred to as a surgical target bone of a patient), in particular, although not limited to, surgery for forming the recess, where a transducer of a bone-anchored hearing aid is to be implanted, in the surface of the temporal bone of the patient; a verification jig for verifying whether or not the recess has been formed as required; and methods for producing these jigs.

BACKGROUND ART

As hearing aids for persons hard of hearing, so-called bone-anchored hearing aids, including transducers, which are implanted in the temporal bones of such persons with hearing difficulty, namely, patients, have been proposed and put to practical use. The bone-anchored hearing aids are effective, particularly, for hearing-impaired patients due to a disorder of the external ear and/or the middle ear, hearing-impaired patients congenitally without formation of the external ear and/or the middle ear, and hearing-impaired patients with a relatively slight disorder of the internal ear. For utilization of such a bone-anchored hearing aid, it is necessary to form a required recess, usually a main recess for accommodation of a transducer and at least two auxiliary recesses (may be referred to hereinafter as sub-recesses) to which fastening screws for fixation of the transducer are to be screwed, in a required site of the surface of the patient's temporal bone, and then to accommodate the transducer in the required site and fix it there. The transducer is an element for vibrating a required weight at a high speed for bone conduction, and needs to have a required mass and a required volume. Thus, the recess for implantation of the transducer needs to be relatively large. The transducer is usually implanted between the temporal lobe of the brain and the sigmoid sinus, a large vein. A relatively large temporal bone exists at such a site and, in the case of a normal temporal bone without congenital malformation and without a past surgical history, surgery for forming the above recess is not necessarily a difficult operation for a skilled doctor. It is often the case, however, that the above-mentioned hearing-impaired patient has congenital temporal bone malformation, congenital middle ear malformation, active middle otitis, or a history of temporal bone surgery. In such a hearing-impaired patient, the accurate and precise formation of the required recess at the required site of the temporal bone is a very difficult operation even for a skilled doctor. To be appropriately aware of which site of the exposed temporal bone the recess should be formed at, and of whether the recess formed is of a required shape is extremely difficult, although not, impossible.

Medical navigation systems displaying the positional relationship between the target site for surgery in a patient during surgery and surgical instruments, such as a surgical knife, a surgical drill, and a robot hand, have been developed as this is well known. Patent Documents 1 and 2 to be cited below each disclose, in connection with such a medical navigation system, a registration template for use in the accurate recognition of the shape of the required site in the patient, for example, the shape of the bone surface; and a method for producing the registration template. No proposals have been made, however, for a surgical jig which is directly used in surgery to make it possible to accurately recognize a position where a recess is to be formed in the surface of a surgical target bone of a patient; and a verification jig for appropriately verifying whether or not the formed recess is of a required shape.

PRIOR ART DOCUMENTS

Patent Documents

Patent Document 1: Japanese Patent No. 4423362
Patent Document 2: WO2012/169642A1

SUMMARY OF THE INVENTION

Problems to be Solved by the Invention

The present invention has been accomplished in the light of the above facts. It is a first technical task of the invention to provide a surgical jig which is directly used in surgery to make it possible to accurately recognize a position where a recess is to be formed in the surface of the surgical target bone of a patient.

It is a second technical task of the invention to provide a verification jig which is directly used in surgery to make it possible to precisely verify whether or not the recess formed in the surface of the surgical target bone of the patient is of a required shape.

It is a third technical task of the invention to provide a combination of the surgical jig and the verification jig described above, accordingly, the combination which is directly used in surgery to make it possible to accurately recognize the position where the recess is to be formed in the surface of the surgical target bone of the patient, and which is directly used in surgery to make it possible to appropriately verify whether or not the recess formed in the surface of the surgical target bone of the patient is of the required shape.

It is a fourth technical task of the invention to provide a method for producing the above-described surgical jig.

It is a fifth technical task of the invention to provide a method for producing the above-described verification jig.

Means for Solving the Problems

According to a first aspect of the present invention, there is provided, as a surgical jig for achieving the above first technical task, a surgical jig for use in surgery for forming a recess in the surface of a surgical target bone of a patient, the surgical jig having an inner surface matching the surface shape of the surgical target bone of the patient, and a penetrating opening formed in correspondence with a site where the recess is to be formed.

In preferred embodiments, the surgical target bone is the temporal bone; the recess includes a main recess for accommodating a transducer of a bone-anchored hearing aid, and at least two sub-recesses to which fastening screws for fixing the transducer are to be screwed; and the penetrating opening includes a main penetrating opening formed in correspondence with a site where the main recess is to be formed, and at least two sub-penetrating openings formed in correspondence with sites where the sub-recesses are to be formed. The outer surface of the surgical jig preferably matches the surface shape of the surgical target bone. Preferably, a cylindrical ridge protruding from the circumferential edge of the penetrating opening is annexed to the outer surface of the surgical jig.

According to a second aspect of the present invention, there is provided, as a verification jig for achieving the above second technical task, a verification jig for verifying whether or not a recess formed in the surface of a surgical target bone of a patient is as required, the verification jig having a protrusion protruding from the inner surface thereof in correspondence with the recess to be formed.

It is preferred for the inner surface of the verification jig to match the surface shape of the surgical target bone of the patient. In preferred embodiments, the surgical target bone is the temporal bone; the recess includes a main recess for accommodating a transducer of a bone-anchored hearing aid, and at least two sub-recesses to which fastening screws for fixing the transducer are to be screwed; and the protrusion includes a main protrusion corresponding to the main recess. Preferably, the outer surface of the verification jig also matches the surface shape of the surgical target bone.

According to a third aspect of the present invention, there is provided, as a combination for achieving the above third technical task, a combination of the above-mentioned surgical jig and the above-mentioned verification jig.

According to a fourth aspect of the present, invention, there is provided, as a method for achieving the above fourth technical task, a method for producing the above-mentioned surgical jig, comprising: obtaining three-dimensional image data concerned with the surface shape of the surgical target bone based on three-dimensional image data generated from tomographic information on the surgical target bone; also obtaining three-dimensional image data concerned with the site where the recess is to be formed; and shaping the surgical jig based on these image data.

According to a fifth aspect of the present invention, there is provided, as a method for achieving the above fifth technical task, a method for producing the above-mentioned verification jig, comprising: obtaining three-dimensional image data concerned with the surface shape of the surgical target bone based on three-dimensional image data generated from tomographic information on the surgical target bone; also obtaining three-dimensional image data concerned with a site where the recess is to be formed, as well as three-dimensional image data concerned with the shape of the recess per se; and shaping the verification jig based on these image data.

Effects of the Invention

When the recess is to be formed in the surface of the surgical target bone of the patient, the surgical jig of the present invention is brought into contact with the surface of the exposed surgical target bone. By so doing, the penetrating opening formed in the surgical jig accurately indicates the site where the recess is to be formed. Then, a surgical tool is caused to act on the surface of the bone through the penetrating opening of the surgical jig, whereby the recess can be formed sufficiently easily and sufficiently accurately. Whether or not the formed recess is a required one can be verified by sinking the protrusion of the verification jig into the formed recess, and the required recess can be formed sufficiently precisely by doing work on the bone until the protrusion is appropriately sunk in. With the method for producing the surgical jig of the present invention, shaping is performed based on the three-dimensional image data concerned with the surface shape of the surgical target bone obtained based on the three-dimensional image data generated from the tomographic information on the surgical target bone, as well as the three-dimensional image data concerned with the site where the recess is to be formed. In this manner, the surgical jig conformed sufficiently precisely to the surface of the surgical target bone of the individual patient is produced. With the method for producing the verification jig of the present invention, on the other hand, shaping is performed based on the three-dimensional image data concerned with the surface shape of the surgical target bone obtained based on the three-dimensional image data generated from the tomographic information on the surgical target bone, as well as the three-dimensional image data concerned with the site where the recess is to be formed, and the three-dimensional image data on the recess per se. In this manner, the verification jig conformed sufficiently precisely to the surface of the surgical target bone of the individual patient is produced.

MODE FOR CARRYING OUT THE INVENTION

Figure 1:
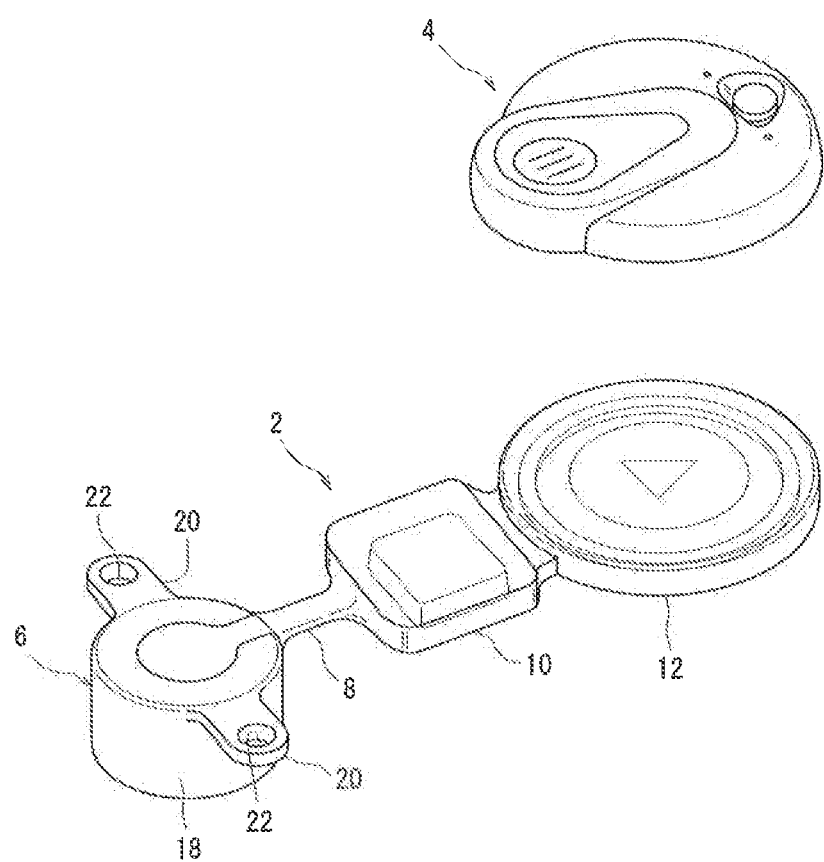
FIG. 1 is a perspective view showing a typical example of a bone-anchored hearing aid.
Figure 2:
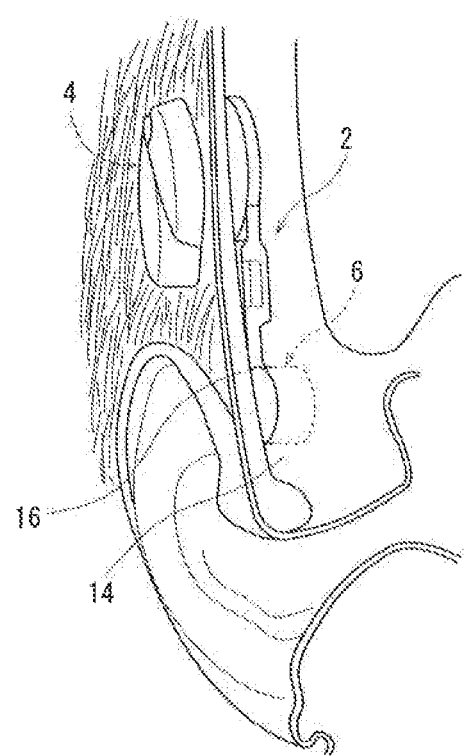
FIG. 2 is a schematic view showing a state where the bone-anchored hearing aid is mounted on a patient.

Prior to detailed explanations for the surgical jig and the verification jig configured in accordance with the present invention, a bone-anchored hearing aid will be mentioned. FIG. 1 illustrates a typical example of the bone-anchored hearing aid. The illustrated hearing aid is composed of an implant body 2 to be implanted in the temple of a patient, and an external auxiliary tool 4 to be mounted on the outer surface of the patient's temple. The implant body 2 has a transducer 6, an electronic package 10 connected to the transducer 6 via a flexible connection 8, and a receiving tool 12 connected to the electronic package 10. The receiving tool 12 includes a coil and a magnet. As will be understood by reference to FIG. 2 along with FIG. 1, the transducer 6 is partially implanted in the temporal bone 14 and fixed to the temporal bone 14, and the connection 8, the electronic package 10, and the receiving tool 12 are accommodated between the temporal bone 14 and the skin 16, as will be described later in further detail. The transducer 6 partly implanted in and fixed to the temporal bone 14 has a disk-shaped main portion 18, and a pair of fastening protruding pieces 20 extending our radially outwardly from the upper end circumferential edge of the main portion 18, and a through-hole 22 is formed in each of the fastening protruding pieces 20. The external auxiliary tool 4, on the other hand, is magnetically attracted to the magnet provided in the receiving tool 12 of the implant body 2, and is thereby held on the outer surface of the patient's temple.

In the above-described bone-anchored, hearing aid, the external auxiliary tool 4 senses a sound, converts it into an electrical signal, and transmits the electrical signal to the receiving tool 12 of the implant body 2. The receiving tool 12 supplies the received electrical signal to the electronic package 10, and the electronic package 10 transmits a vibration signal to the transducer 6 in response to the received electrical signal to vibrate the transducer 6. The vibration of the transducer 6 is transmitted to the internal ear (not shown) through the temporal bone 14. Electrical power supply to the implant body 2 is also performed via the receiving tool 12 from the external auxiliary tool 4. The present invention does not relate to such a bone-anchored hearing aid itself, and the bone-anchored hearing aid per se is one of a well-known form marketed under the trade name "BONEBRIDGE" by MED-EL Medical Electronics in Austria. Hence, a detailed description of this bone-anchored hearing aid itself is omitted herein.

Figure 3:
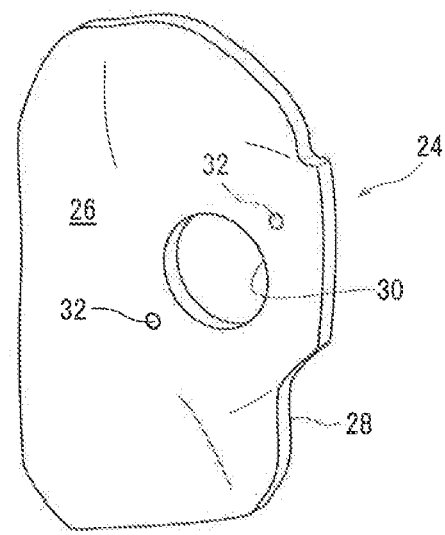
FIG. 3 is a perspective view showing a preferred embodiment of a surgical jig configured in accordance with the present invention.

FIG. 3 illustrates a preferred embodiment of a surgical jig constituted in accordance with the present invention, which can be used in forming a recess in the surface of the temporal bone 14 of a patient in order to partly implant the transducer 6 of the implant body 2 of the above-described bone-anchored hearing aid into the temporal bone 14 of the patient. The illustrated surgical jig, indicated entirely at the numeral 24, importantly has an inner surface 26 of a shape matching the surface shape of the surgical target bone of the patient, which, in the illustrated embodiment, is the surface shape of the temporal bone 14 of the patient. From the point of view of avoiding a sense of incongruity in surgical procedures to be described later, it is preferred that the outer surface 28 of the surgical jig 24 also be of a shape matching the surface shape of the surgical target bone of the patient, or in the illustrated embodiment, the surface of the temporal bone 14 of the patient. Accordingly, it is preferred for the inner surface 26 and the outer surface 23 of the surgical jig 24 to extend substantially in parallel. (In using a verification jig to be described later, in a state superposed on the surgical jig 24, moreover, it is advantageous that the outer surface 28 of the surgical jig 24 also be of a shape matching the surface shape of the surgical target bone of the patient, or in the illustrated embodiment, the surface of the temporal bone 14 of the patient, and that the inner surface of the verification jig to be described later also be of a shape matching the surface shape of the surgical target bone of the patient, or in the illustrated embodiment, the surface of the temporal bone 14 of the patient.) In the surgical jig 24, it is important that a penetrating opening be further formed in correspondence with the site of a recess to be formed in the surface of the surgical target bone of the patient. In the illustrated embodiment, a main penetrating opening 30 is formed in correspondence with a site where a main recess (the main recess will be further mentioned later) for accommodating the disk-shaped main portion 18 of the transducer 6 in the implant body 2 is to be formed, and two auxiliary penetrating openings (may be referred to hereinafter as sub-penetrating openings) 32 are formed in correspondence with sites where sub-recesses to be threadedly engaged with fastening screws to be inserted through the through-holes 22 of the two fastening protruding pieces 20 are to be formed (the fastening screw and the sub-recess will be further mentioned later). Advantageously, the inner diameter of the main penetrating opening 30 is slightly larger than the outer diameter of the disk-shaped main portion 18 of the transducer 6, whereas the inner diameter of the sub-penetrating opening 32 is slightly larger than the inner diameter of the through-hole 22. For convenience in the surgical procedures as will be described later, it is advantageous for the surgical jig 24 to be transparent or translucent.

Next, an explanation will be offered for a preferred method for producing the surgical jig 24 as described above. First of all, three-dimensional image data on the surface shape of the surgical target bone of the patient, or in the illustrated embodiment, the surface shape of the temporal bone 14, are obtained. Such three-dimensional image data can be generated based on tomographic image information acquired from slice images, by CT, MRI or the like, of a site including the surgical target bone of the patient. Then, which site in the surface of the surgical target bone of the patient is an appropriate site, from the medical point of view, for partial implantation of the disk-shaped main portion 18 of the transducer 6 is investigated, and three-dimensional image data on such a site are obtained. Based on these three-dimensional image data, the surgical jig 24 is shaped by a suitable stereoscopic shaping method. Examples of the suitable stereoscopic shaping method are stereolithography, inkjet rapid prototyping, powder shaping, powder sintering additive manufacturing, laminated object manufacturing, and selective laser sintering. Any biocompatible materials can be used as the materials for shaping the surgical jig 24 and, for example, suitable synthetic resins, synthetic rubbers, suitable inorganic materials, and composite materials containing inorganic material powders and synthetic resins can be used.

Figure 4:
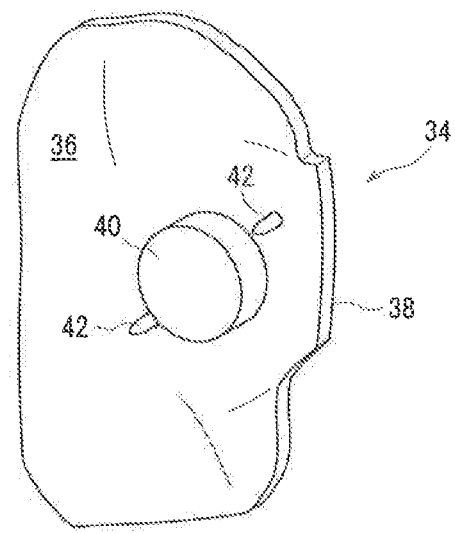
FIG. 4 is a perspective view showing a preferred embodiment of a verification jig configured in accordance with the present invention.

FIG. 4 illustrates a preferred embodiment of a verification jig configured in accordance with the present invention, which is designed to verify whether or not the recess formed in the surface of the patient's temporal bone 14 is as required. The verification jig, indicated entirely at the numeral 34, preferably has an inner surface 36 of a shape matching the surface shape of the surgical target bone of the patient, or in the illustrated embodiment, the surface of the temporal bone 14 of the patient, as does the aforementioned surgical jig 24. From the point of view of avoiding a sense of incongruity in the surgical procedures to be described later, it is preferred that the outer surface 38 of the verification jig 34 also be of a shape matching the surface shape of the surgical target bone of the patient, or in the illustrated embodiment, the surface of the temporal bone 14 of the patient. Accordingly, it is preferred for the inner surface 36 and the outer surface 38 of the verification jig 34 to extend substantially in parallel. In the verification jig 34, it is important that a protrusion protruding from the inner surface 36 be further formed in correspondence with the recess to be formed in the surface of the surgical target bone of the patient. In the illustrated embodiment, a main protrusion 40 protruding from the inner surface 36 is formed in correspondence with the main recess (the main recess will be further mentioned later) for accommodating the disk-shaped main portion 18 of the transducer 6 in the implant body 2, and two auxiliary protrusions (may be referred to hereinafter as sub-protrusions) 42 protruding from the inner surface 36 are formed in correspondence with the sub-recesses to be threadedly engaged with the fastening screws to be inserted through the through-holes 22 of the two fastening protruding pieces 20 (the fastening screw and the sub-recess will be further mentioned later). The outer diameter of the main protrusion 40 may be substantially the same as the outer diameter of the disk-shaped main portion 18 of the transducer 6. The protruding length of the main protrusion 40 is advantageously the sum of the length from the lower surface of the fastening protruding piece 20 to the leading end, i.e. the lower end, of the disk-shaped main portion 18 of the transducer 6 and the thickness of the surgical jig 24. Each of the sub-protrusions 42 is of a conical shape which has a base end of substantially the same diameter as the inner diameter of the through-hole 22 of the fastening protruding piece 20 (the length of the base end is substantially the same as the thickness of the surgical jig 24) and whose outer diameter gradually decreases, starting at the base end, toward the leading end. The protruding length of the sub-protrusion 42 can be set, as appropriate, in accordance with the length of the fastening screw. If desired, the shape of the sub-recess itself need not necessarily be accurate, but may be one into which the fastening screw can be screwed. Thus, it is possible to refrain from forming the two sub-protrusions 42 on the inner surface 36 of the verification jig 34, or holes for visually confirming the formation of the sub-recesses can be formed instead of the formation of the two sub-protrusions 42. For convenience in the surgical procedures as will be described later, the verification jig 34, like the surgical jig 24, is also advantageously transparent or translucent.

The above-described verification jig 34 can be produced by a manufacturing method remarkably similar to the manufacturing method for the surgical jig 24. That is, the verification jig 34 can be produced, by a suitable stereoscopic shaping method based on three-dimensional image data on the surface shape of the surgical target bone of the patient, or in the illustrated embodiment, the surface shape of the temporal bone 14; three-dimensional image data on the site where the recess (main recess and sub-recesses) should be formed; and three-dimensional image data on the recess (main recess and sub-recesses) per se. The material for shaping the verification jig 34, like the material for shaping the surgical jig 24, may also be any biocompatible material, and can be exemplified by a suitable synthetic resin, synthetic rubber, a suitable inorganic material, or a composite material containing an inorganic material powder and synthetic resin.

Figure 5:
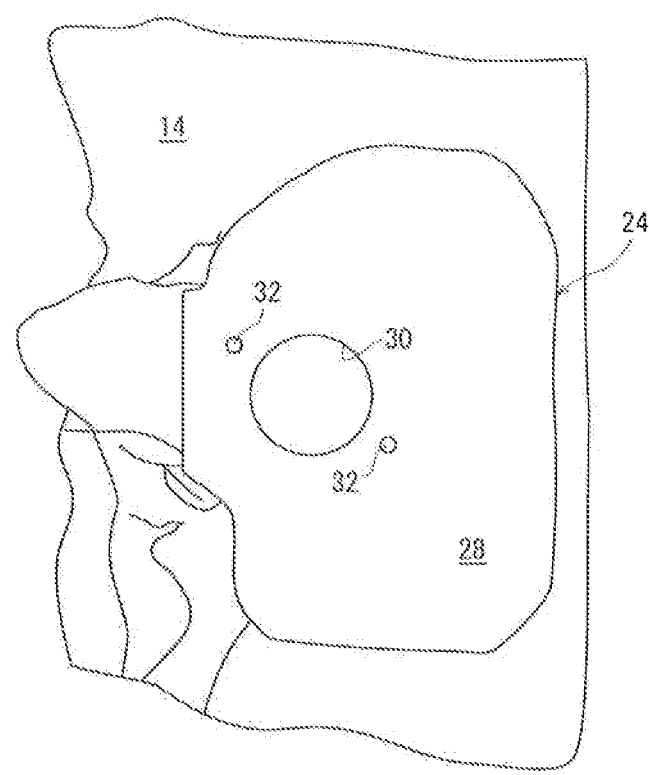
FIG. 5 is a front view showing the manner of use of the surgical jig shown in FIG. 3.
Figure 6:
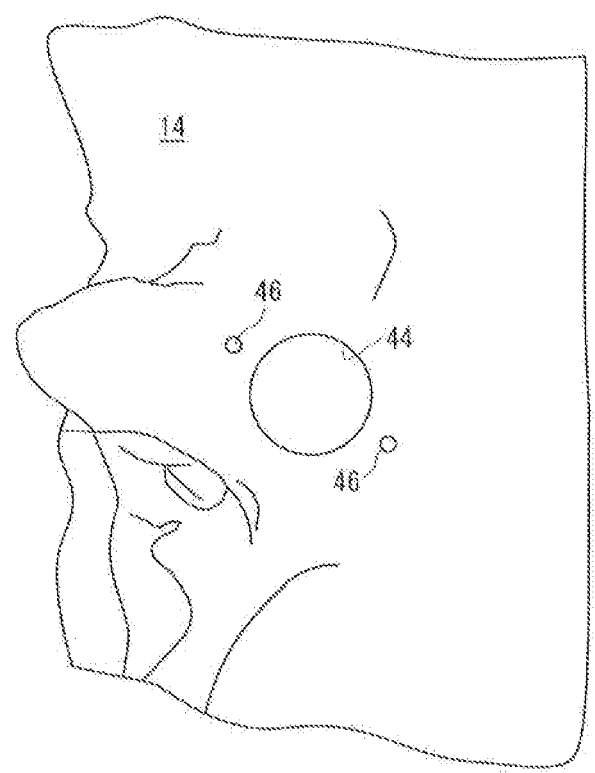
FIG. 6 is a front view showing a recess formed in the surface of the temporal bone of the patient.
Figure 8:
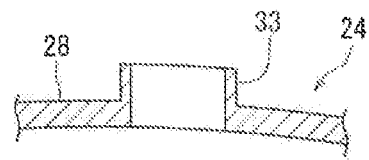
FIG. 8 is a partial sectional view showing a modification of the surgical jig.

Next, a typical example of surgical procedures utilizing the surgical jig 24 and the verification jig 34 described above will be explained. By reference to FIG. 5, during surgery for implanting the implant body 2 of the bone-anchored hearing aid in the temple of the patient, the temple of the patient is incised to expose a required region of the temporal bone 14. The surgical jig 24 is brought into intimate contact with the surface of the exposed temporal bone 14. Since the inner surface 26 of the surgical jig 24 matches the surface shape of the temporal bone 14, the surgical jig 24 has its inner surface 26 in intimate contact with the surface of the temporal bone 14 without gap. Then, the required recess, composed of one main recess and two sub-recesses, is formed in the surface of the temporal bone 14. On this occasion, the temporal bone 14 is cut through the main penetrating opening 30 formed in the surgical jig 24 to form a main recess 44 (see FIG. 6), and the temporal bone 14 is cut through the two sub-penetrating openings 32 to form two sub-recesses 46. The site of formation and dimensions of the main recess 44 are clearly regulated by the main penetrating opening 30, while the site of formation and dimensions of the two sub-recesses 46 are clearly regulated by the two sub-penetrating openings 32. Thus, the main recess 44 and the two sub-recesses 46 can be formed sufficiently easily and precisely. If desired, a regulating flange is annexed to a cutting drill, and the regulating flange is contacted with the outer surface 28 of the surgical jig 24, whereby the main recess 44 can be reliably prevented from being cut to an excessive depth. In this case, as shown in FIG. 8, a cylindrical ridge 33 protruding from the circumferential edge of the main penetrating opening 30 can be formed integrally on the outer surface 28 of the surgical jig 24, and the above regulating flange of the cutting drill can be contacted with such a ridge 33. Furthermore, a cylindrical sleeve separately formed can be fixed to the inside of the main penetrating opening 30, and such a sleeve can be allowed to protrude on the side of the outer surface 28 of the surgical jig 24. Whether the depths of the resulting main recess 44 and two sub-recesses 46 are appropriate or not can be judged by superposing the verification jig 34 on the outer surface 28 of the surgical jig 24 to insert the main protrusion 40 and two sub-protrusions 42 of the verification jig 34 into the resulting main recess 44 and two sub-recesses 46. If the main protrusion 40 and two sub-protrusions 42 of the verification jig 34 are inserted sufficiently tightly into the resulting main recess 44 and two sub-recesses 46, it follows that the formation of the required main recess 44 and two sub-recesses 46 has been verified. Instead of superposing the verification jig 34 on the surgical jig 24 to insert the main protrusion 40 and the two sub-protrusions 42 of the verification jig 34 into the main recess 44 and the two sub-recesses 46, it is permissible to release the surgical jig 24 from the surface of the temporal bone 14, and then directly bring the verification jig 34 into close contact with the temporal bone 14, thereby inserting the main protrusion 40 and the two sub-protrusions 42 of the verification jig 34 into the main recess 44 and the two sub-recesses 46. (In this case, the protruding lengths of the main protrusion 40 and the two sub-protrusions 42 are advantageously the differences when the thickness of the surgical jig 24 is subtracted from the protruding lengths in the illustrated embodiment.)

Figure 7:
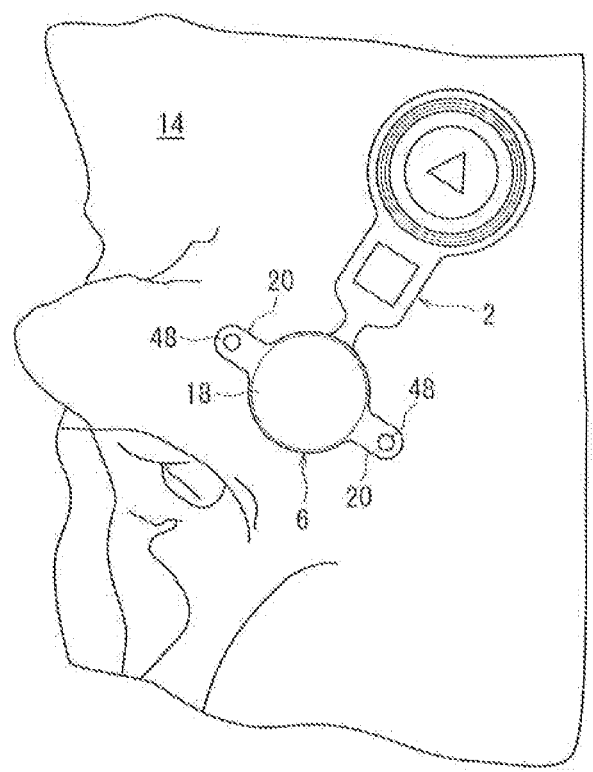
FIG. 7 is a front view showing a state in which an implant body of the bone-anchored hearing aid shown in FIG. 1 is mounted on the patient.

After the formation of the main recess 44 and the two sub-recesses 46 as required is verified, the verification jig 34 and the surgical jig 24 are released from the site on the surface of the temporal bone 14. Then, as shown in FIG. 7, the disk-shaped main portion 18 of the transducer 6 of the implant body 2 is accommodated within the main recess 44, and the respective through-holes 22 formed in the two fastening protruding pieces 20 in close contact with the surface of the temporal bone 14 are aligned with the two sub-recesses 46. Then, fastening screws 48 are screwed to the temporal bone 14 through the through-holes 22 of the fastening protruding pieces 20, whereby the transducer 6 is fixed to the temporal bone 14. The connection 8, the electronic package 10, and the receiving tool 12 of the implant body 2 are accommodated between the temporal bone 14 and the skin 16. Then, the incised skin 16 is sutured.

EXPLANATIONS OF LETTERS OR NUMERALS

2: Implant body of bone-anchored hearing aid
4: External auxiliary tool of bone-anchored hearing aid
6: Transducer
14: Temporal bone of patient
18: Disk-shaped main portion of transducer
20: Fastening protruding piece of transducer
22: Through-hole
24: Surgical jig
26: Inner surface of surgical jig
28: Outer surface of surgical jig
30: Main penetrating opening
32: Sub-penetrating opening
33: Cylindrical ridge
34: Verification jig
36: Inner surface of verification jig
38: Outer surface of verification jig
40: Main protrusion
42: Sub-protrusion
44: Main recess
46: Sub-recess

The invention claimed is:
1. A surgical jig for use in surgery for forming a recess in a surface of a temporal bone as a surgical target bone of a patient, the recess including a main recess for accommodat- ing a transducer of a bone-anchored hearing aid, and at least two sub-recesses in which fastening screws for fixing the transducer are received, the surgical jig having an inner surface matching a surface shape of the surgical target bone of the patient, and a penetrating opening at a site where the recess is to be formed, the penetrating opening including a main penetrating opening where the main recess is to be formed, and at least two sub-penetrating openings where the sub-recesses are to be formed.

2. The surgical jig according to claim 1, wherein
an outer surface of the surgical jig also matches the surface shape of the surgical target bone.

3. The surgical jig according to claim 1, wherein
a cylindrical ridge protruding from a circumferential edge of the penetrating opening is annexed to an outer surface of the surgical jig.

\* \* \* \* \*